(12) United States Patent
Arnold, Jr.

(10) Patent No.: US 10,179,931 B2
(45) Date of Patent: *Jan. 15, 2019

(54) METHODS FOR IMMOBILIZING TARGET NUCLEIC ACIDS UTILIZING COMBINATORIAL CAPTURE PROBES

(71) Applicant: Lyle J. Arnold, Jr., Poway, CA (US)

(72) Inventor: Lyle J. Arnold, Jr., Poway, CA (US)

(73) Assignee: AEGEA BIOTECHNOLOGIES, INC.

( * ) Notice: Subject to any disclaimer, the term of this patent is extended or adjusted under 35 U.S.C. 154(b) by 0 days.

This patent is subject to a terminal disclaimer.

(21) Appl. No.: 15/652,372

(22) Filed: Jul. 18, 2017

(65) Prior Publication Data
US 2018/0010173 A1   Jan. 11, 2018

Related U.S. Application Data

(62) Division of application No. 14/214,684, filed on Mar. 15, 2014, now Pat. No. 9,738,925.

(60) Provisional application No. 61/801,040, filed on Mar. 15, 2013.

(51) Int. Cl.
*C12P 19/34* (2006.01)
*C12Q 1/6834* (2018.01)

(52) U.S. Cl.
CPC .................. *C12Q 1/6834* (2013.01)

(58) Field of Classification Search
CPC ............ C12Q 1/6834; C12Q 2525/161; C12Q 2525/301; C12Q 2537/162
USPC ........................................................ 435/91.2
See application file for complete search history.

(56) References Cited

U.S. PATENT DOCUMENTS

| | | | | |
|---|---|---|---|---|
| 6,573,048 B1* | 6/2003 | VanAtta | ............... | C12Q 1/6816 435/6.1 |
| 2012/0115744 A1* | 5/2012 | Raymond | ............ | C12Q 1/6811 506/9 |
| 2014/0370506 A1* | 12/2014 | Carlson | ................ | C12Q 1/6816 435/6.11 |

* cited by examiner

*Primary Examiner* — Cynthia B Wilder
(74) *Attorney, Agent, or Firm* — David B. Waller

(57) ABSTRACT

The present invention provides methods for immobilizing target nucleic acids on a solid support utilizing combinatorial capture probe pairs. These pairs contain first and second capture oligonucleotides that each comprise a target binding region, a capture region and a stem region positioned between the target binding and capture regions. The target binding regions comprise nucleic acid sequences that allow them to hybridize to adjacent regions on the target nucleic acid. The stem regions have nucleic acid sequences that are complementary to each other and the capture regions each comprise a sequence that when positioned adjacent to one another produce a combined nucleic acid sequence that is complementary to a portion of an oligonucleotide bound to a solid support. When the first and second capture oligonucleotides are annealed to the target nucleic acid, the stem regions are brought together allowing them to hybridize, which in turn brings the capture regions together to produce a combined nucleic acid sequence. This combined nucleic acid sequence is then able to hybridize to the oligonucleotide bound to the solid support thereby immobilizing the target nucleic acid.

3 Claims, 1 Drawing Sheet

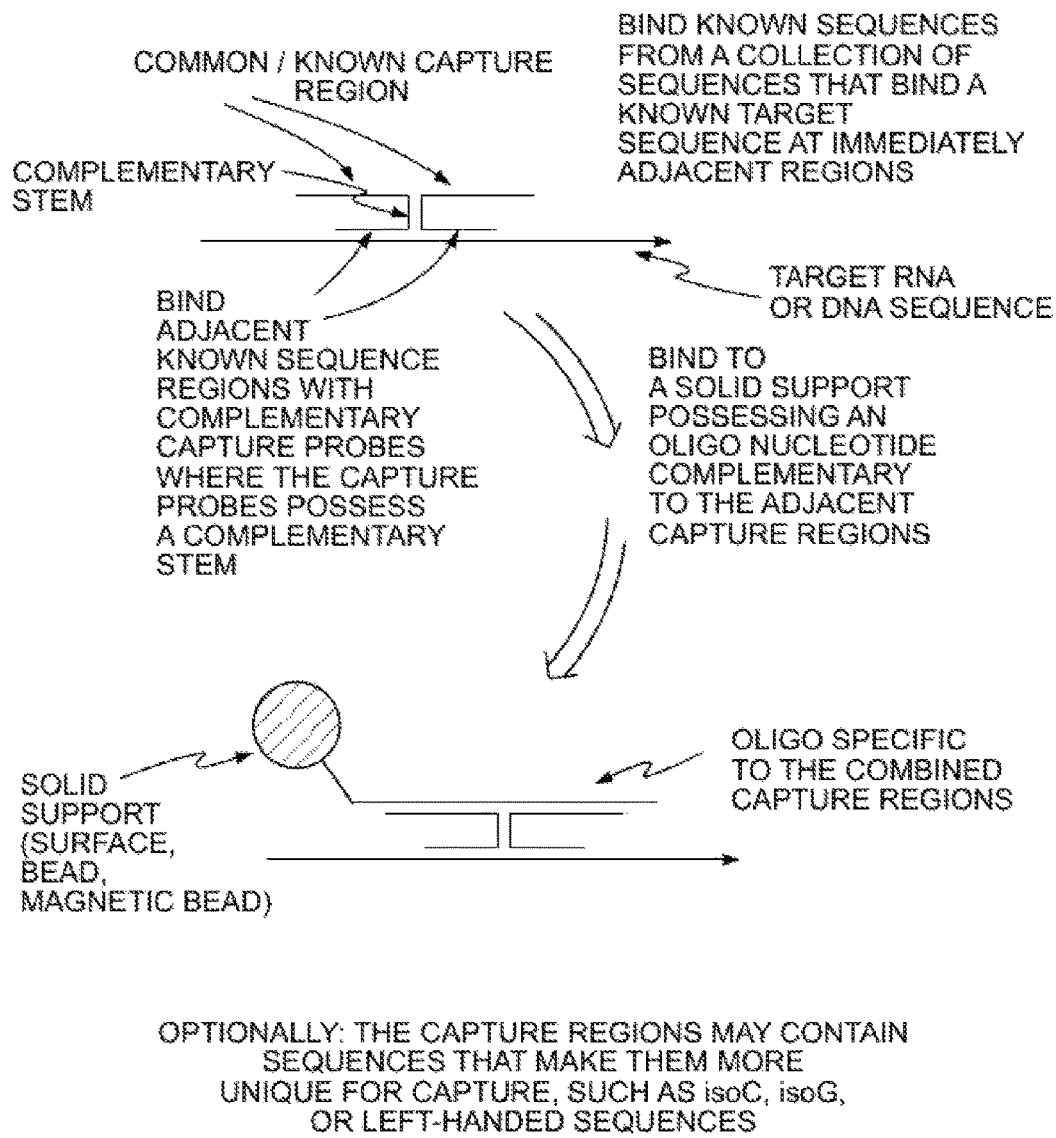

METHODS FOR IMMOBILIZING TARGET NUCLEIC ACIDS UTILIZING COMBINATORIAL CAPTURE PROBES

CROSS-REFERENCE TO RELATED APPLICATIONS

This application is a divisional of application Ser. No.: 14/214,684, now U.S. patent No.: 9,738,925.

This application is a non-provisional patent application of provisional patent application Ser. No. 61/801,040 filed Mar. 15, 2013 incorporated herein in its entirety.

STATEMENT REGARDING FEDERALLY SPONSORED RESEARCH OR DEVELOPMENT

None

INCORPORATION-BY-REFERENCE OF MATERIAL SUBMITTED ON COMPACT DISC

None

BACKGROUND OF THE INVENTION (1) Field of the Invention

The present invention relates to methods of immobilizing target nucleic acids on a solid support. Specifically, methods that utilize combinatorial capture probe pairs to immobilize specific target nucleic acids or groups of specific target nucleic acids on a solid support.

(2) Description of Related Art

Typical prior-art methods use specifically synthesized single natural deoxyoligonucleotides to capture target sequences of interest. These target capture method can capture sequences closely or even distantly related sequences that compromise the efficiency and purity with which specific targets can be captured. What is needed are methods that provide even higher levels of specificity and efficiency.

Compared to other methods, this invention offers benefits of speed, efficiency, and significantly enhanced specificity of capture.

BRIEF SUMMARY OF THE INVENTION

The present invention provides methods for immobilizing target nucleic acids on a solid support utilizing combinatorial capture probe pairs.

One aspect of the present invention mixes a capture oligonucleotide pair containing first and second capture oligonucleotides with a target nucleic acid(s). Each capture oligonucleotide comprises a target binding region and a tag region, the tag region comprising a capture region and a stem region positioned between the target binding and capture regions. The target binding regions comprise nucleic acid sequences that allow them to hybridize to adjacent regions on the target nucleic acid. The stem regions have nucleic acid sequences that are complementary to each other and the capture regions each comprise a sequence that when positioned adjacent to one another produce a combined nucleic acid sequence that is complementary to a portion of an oligonucleotide bound to a solid support or an oligonucleotide in solution which is later bound to a solid support. The first and second capture oligonucleotides are annealed to the target nucleic acid, which brings the stem regions in close proximity to allow them to hybridize. When the stem regions hybridize this brings the capture regions together to produce a combined nucleic acid sequence. This sequence is then hybridized to the oligonucleotide bound to the solid support (or in solution, which is subsequently bound to a solid support) thereby immobilizing the target nucleic acid on the solid support. The capture region of a single capture oligonucleotide by itself does not possess sufficient affinity for the oligonucleotide bound to the solid support or in solution to remain stably bound under the selected assay conditions. However, when two capture regions are brought together as described above, the combined capture regions bind stably to the oligonucleotide bound to the solid support or in solution under the selected assay conditions.

Other aspects of the invention are found throughout the specification.

BRIEF DESCRIPTION OF THE DRAWINGS

FIG. 1 is a schematic diagram of one aspect of the present invention.

DETAILED DESCRIPTION OF THE INVENTION

Unless defined otherwise, all terms used herein have the same meaning as are commonly understood by one of skill in the art to which this invention belongs. All patents, patent applications and publications referred to throughout the disclosure herein are incorporated by reference in their entirety. In the event that there is a plurality of definitions for a term herein, those in this section prevail.

The term "oligonucleotide" as used herein refers to a polymeric form of nucleotides, either ribonucleotides or deoxyribonucleotides, incorporating natural and non-natural nucleotides of a length ranging from at least 2, or generally about 5 to about 200, or more commonly to about 100. Thus, this term includes double- and single-stranded DNA and RNA.

The term "target," "target sequence," or "target nucleic acid" as used herein refers to a nucleic acid that contains a polynucleotide sequence of interest, for which purification, isolation, capture, immobilization, amplification, identification, detection, quantitation, mass determination and/or sequencing, and the like is/are desired. The target sequence may be known or not known, in terms of its actual sequence and may be synthetic or obtained from a biological sample.

The term "primer" or "primer sequence" as used herein are nucleic acids comprising sequences selected to be substantially complementary to each specific sequence to be amplified. More specifically, primers are sufficiently complementary to hybridize to their respective targets. Therefore, the primer sequence need not reflect the exact sequence of the target. Non-complementary bases or longer sequences can be interspersed into the primer, provided that the primer sequence has sufficient complementarity with the sequence of the target nucleic acid to permit hybridization and extension.

The term "support" or "solid support" refers to conventional supports that include, for example, polymers such as microtiter wells, beads, particles or fibers, and silane or silicate supports such as glass slides or tubes to which capture molecules, for example, oligonucleotides are covalently or non-covalently bound.

The term "sample" as used herein refers to essentially any sample containing the desired target nucleic acid(s), including but not limited to tissue or fluid isolated from a human being or an animal, including but not limited to, for example, blood, plasma, serum, spinal fluid, lymph fluid, tears or saliva, urine, semen, stool, sputum, vomit, stomach aspirates, bronchial aspirates, organs, muscle, bone marrow, skin, tumors and/or cells obtained from any part of the organism; plant material, cells, fluid, etc.; an individual bacterium, groups of bacteria and cultures thereof; water; environmental samples, including but not limited to, for example, soil water and air; semi-purified or purified nucleic acids from the sources listed above, for example; nucleic acids that are the result of a process, such as template formation for sequencing, including next generation sequencing, sample processing, nuclease digestion, restriction enzyme digestion, replication, and the like.

The term "amplifying" or "amplification" as used herein refers to the process of creating nucleic acid strands that are identical or complementary to a complete target nucleic acid sequence, or a portion thereof, or a universal sequence that serves as a surrogate for the target nucleic acid sequence. The term "identical" as used herein refers to a nucleic acid having the same or substantially the same nucleotide sequence as another nucleic acid.

The term "affixed" as used herein refers to the attachment of a molecule(s), such as an oligonucleotide, to a solid support. A wide variety of methods commonly known in the art can be used for attachment. One preferred method is covalent attachment.

The term "nucleic acid" or "nucleic acid sequence" as used herein refers to a polynucleotide compound, which includes oligonucleotides, comprising nucleosides or nucleoside analogs that have nitrogenous heterocyclic bases or base analogs, covalently linked by standard phosphodiester bonds or other linkages. Nucleic acids include RNA, DNA, chimeric DNA-RNA polymers or analogs thereof. In a nucleic acid, the backbone may be made up of a variety of linkages, including one or more of sugar-phosphodiester linkages, peptide-nucleic acid (PNA) linkages (PCT No. WO 95/32305), phosphorothioate linkages, methylphosphonate linkages, or combinations thereof. Sugar moieties in a nucleic acid may be ribose, deoxyribose, or similar compounds with substitutions, e.g., 2' methoxy and 2' halide (e.g., 2'-F.) substitutions.

Nitrogenous bases may be conventional bases (A, G, C, T, U), non-natural nucleotides such as isocytosine and isoguanine, analogs thereof (e.g., inosine; The Biochemistry of the Nucleic Acids 5-36, Adams et al., ed., 11th ed., 1992), derivatives of purine or pyrimidine bases (e.g., $N^4$-methyl deoxyguanosine, deaza- or aza-purines, deaza- or aza-pyrimidines, pyrimidines or purines with altered or replacement substituent groups at any of a variety of chemical positions, e.g., 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, or pyrazolo-compounds, such as unsubstituted or 3-substituted pyrazolo[3,4-d]pyrimidine (e.g. U.S. Pat. Nos. 5,378,825, 6,949,367 and PCT No. WO 93/13121). Nucleic acids may include "abasic" positions in which the backbone does not have a nitrogenous base at one or more locations (U.S. Pat. No. 5,585,481), e.g., one or more abasic positions may form a linker region that joins separate oligonucleotide sequences together.

A nucleic acid may comprise only conventional sugars, bases, and linkages as found in conventional RNA and DNA, or may include conventional components and substitutions (e.g., conventional bases linked by a 2' methoxy backbone, or a polymer containing a mixture of conventional bases and one or more analogs). The term includes "locked nucleic acids" (LNA), which contain one or more LNA nucleotide monomers with a bicyclic furanose unit locked in a RNA mimicking sugar conformation, which enhances hybridization affinity for complementary sequences in ssRNA, ssDNA, or dsDNA (Vester et al., 2004, Biochemistry 43(42):13233-41).

The term "hybridization," "hybridize," "anneal" or "annealing" as used herein refers to the ability, under the appropriate conditions, for nucleic acids having substantial complementary sequences to bind to one another by Watson & Crick base pairing. Nucleic acid annealing or hybridization techniques are well known in the art. See, e.g., Sambrook, et al., Molecular Cloning: A Laboratory Manual, Second Edition, Cold Spring Harbor Press, Plainview, N.Y. (1989); Ausubel, F. M., et al., Current Protocols in Molecular Biology, John Wiley & Sons, Secaucus, N.J. (1994). The term "substantial complementary" as used herein refers both to complete complementarity of binding nucleic acids, in some cases referred to as an identical sequence, as well as complementarity sufficient to achieve the desired binding of nucleic acids. Correspondingly, the term "complementary hybrids" encompasses substantially complementary hybrids.

The term "releasing" or "released" as used herein refers to separating the desired amplified nucleic acid from its template by heating the duplex to a temperature that denatures the nucleic acid duplex forming two separate oligonucleotide strands.

The term "removing" as used herein refers to a variety of methods used to isolate or otherwise remove and separate one nucleic acid strand of a duplex from another, such as for example enzymatic, thermal and/or chemical digestion, degradation and/or cleavage of one of the strands of the duplex, or denaturation/dissociation of the strands by heat, acoustic energy, chemicals, enzymes or a combination thereof.

The terms "tag region" or "tag sequence" refer to a user-defined nucleic acid sequence or sequences that are incorporated into an oligonucleotide or other nucleic acid structure, such as a primer, to provide one or more desired functionalities. Examples of such elements include, for example, adapters, sequencing primers, amplification primers, capture and/or anchor elements, hybridization sites, promoter elements, restriction endonuclease site, detection elements, mass tags, barcodes, binding elements, and/or non-natural nucleotides. Other elements include those that clearly differentiate and/or identify one or more nucleic acids or nucleic acid fragments in which a tag sequence has been incorporated from other nucleic acids or nucleic acid fragments in a mixture, elements that are unique in a mixture of nucleic acids so as to minimize cross reactivity and the like and elements to aid in the determination of sequence orientation. Some or all of the elements in a tag sequence can be incorporated into amplification products.

General methods for amplifying nucleic acid sequences have been well described and are well known in the art. Any such methods can be employed with the methods of the present invention. In some embodiments, the amplification uses digital PCR methods, such as those described, for example, in Vogelstein and Kinzler ("Digital PCR," *PNAS*, 96:9236-9241 (1999); incorporated by reference herein in its entirety). Such methods include diluting the sample containing the target region prior to amplification of the target region. Dilution can include dilution into conventional plates, multiwell plates, nanowells, as well as dilution onto micropads or as microdroplets. (See, e.g., Beer N R, et al., "On-chip, real time, single copy polymerase chain reaction in picoliter droplets," *Anal. Chem.* 79(22):8471-8475 (2007); Vogelstein and Kinzler, "Digital PCR," *PNAS*, 96:9236-9241 (1999); and Pohl and Shih, "Principle and applications of digital PCR," *Expert Review of Molecular Diagnostics,* 4(1):41-47 (2004); all of which are incorporated by reference herein in their entirety.) In some embodiments, the amplification is by digital PCR.

In some cases, the enzymes employed with the methods of the present invention for amplification of the target region include but are not limited to high-fidelity DNA polymerases, for example DNA polymerases that have 3'-5' exonuclease proof-reading capabilities. Examples of enzymes that can be used with the methods include but are not limited to AmpliTaq, Phusion HS II, Deep Vent, and Kapa HiFi DNA polymerase.

High-fidelity enzymes allow for high-fidelity (highly accurate) amplification of a target sequence. In some embodiments, the enzymes employed will include high-fidelity DNA polymerases, for example DNA polymerases that have 3'-5' exonuclease proofreading capabilities. Enzymes that can be used with the methods include but are not limited to AmpliTaq, Phusion HS II, Deep Vent, and Kapa HiFi DNA polymerase.

The amplification product can be detected/analyzed using a number of methods known to those skilled in the art including, but not limited to, fluorescence, electrochemical detection, gel analysis and sequencing. Furthermore, the product can be quantitated using a number of methods known to those skilled in the art such as real time amplification. Quantitation can be normalized by comparison to so-called "house-keeping genes" such as actin or GAPDH or to an internal control that can be added to the reaction in a known amount. Such methods are well known and have been described in Sambrook and Russell, *Molecular Cloning: A Laboratory Manual* (3rd Ed.) (2001).

Instrumentation for performing the methods described herein is readily available. Such instruments can include instruments for real-time and end-point PCR assays, emulsion PCR, solid-phase PCR, melting curve analyses, and sequencing analyses. Such instruments include the 7500 Fast Dx real-time instrument, which is capable of high-resolution melting curve analyses (Life Technologies, Carlsbad, Calif.) and the 3500xl capillary gel instruments. Other instruments known in the art to be useful in the methods of the present invention are also contemplated for use by one of skill in the art in practicing the methods of the present invention.

The present invention provides methods for immobilizing target nucleic acids on a solid support utilizing combinatorial capture probe pairs to enhance capture of nucleic acids. These probes may be prepared for capturing specific target nucleic acids or groups of specific target nucleic acids.

In one mode of this invention, a pre-synthesized library of respective library members can be immediately assembled to capture a wide array of nucleic acid targets by simply combining the appropriate library members. In this mode, there is no delay in capturing a large number of sequences without the need to synthesize target specific sequences. In another mode, this invention provides for methods of capturing target sequences with much higher specificity using a common immobilization system. Using the recognition of specific sites for capture, based on the combined assembly of at least two elements, specificity is increased. Each element has high specificity owning to the fact that each of the binding interactions binds with high specificity and when used in combination, specificity is increased even higher. Each of the oligonucleotides bind target sequences with relatively short binding domains. If either of the oligonucleotides is not bound to the target, capture does not occur. Thus specificity is driven by the specificity of the first binding oligonucleotide multiplied by the binding specificity of the second binding oligonucleotide. At the same time, once bound immediately next to each other a longer, unique sequence is formed that can be recognized by an immobilization oligonucleotide with extremely high specificity. This benefit can be enhanced by utilizing nucleotide analogs in the immobilization sequence that do not occur in natural nucleic acid sequences. For example, isoCytosine (isoC) and isoGuanine (isoG) analogs can be employed that do not bind natural nucleic acids. Additionally, completely unnatural strands can be formed to drive immobilization, like left-handed helixes that do not hybridize with natural nucleic acid sequences. Thus this invention permits the use of absolutely specific binding partners that have no opportunity of non-specifically interacting with native wild-type sequences. This adds significantly to the efficiency and specificity of capture.

In one aspect of the present invention, the capture probe pair comprising a first and second capture oligonucleotide are generated, each comprising a target binding region and a tag region, the tag region comprising a capture region and a stem region positioned between the target binding and capture regions. The target binding regions of the first and second capture oligonucleotides have sequences that allow them to hybridize adjacent to one another on the target nucleic acid. The stem regions of the first and second oligonucleotide pair are complementary so that following hybridization, the stem regions hybridize forming a stable stem duplex. Prior to hybridization of the capture oligonucleotides to the target nucleic acid, duplex formation does not occur because hybridization of the stem region in solution is not stable.

When the capture oligonucleotides are hybridized to the target nucleic acid and the stem regions from a stable duplex the capture regions are brought into close proximity to produce a combined capture sequence or tag. Optionally, binding of the target binding regions to the target can be performed under low stringency conditions to increase target nucleic acid binding and the capture step can be performed under high stringency conditions.

In another embodiment multiple pairs of first and second capture oligonucleotides may be used in a sample to either hybridize different regions of a target nucleic, bind to multiple target nucleic acids or both.

In a further embodiment, the combined capture sequence resulting from the close proximity of the capture regions of the capture oligonucleotides may be common to all capture oligonucleotide pairs, different for each pair, or a combination thereof. The capture oligonucleotide pairs may be preselected for desired capture prior to use.

In a third embodiment, the stem and capture portions of the specific binding oligonucleotides may contain a wide variety of analogs. These include, but are not limited to, 2'-OMe, 2'-F, LNA, PNA, isoC, isoG and left-handed helical conformations. For example, the stem sequences of both capture oligonucleotides of a pair may contain 2'-OMe residues. This increases the binding strength of the stem duplex and allows for shorter designs for these regions. Typically discrimination between the bound and unbound forms is also increased (i.e., stability difference between the stem segments in solution and the stem formed when both capture oligonucleotides hybridize to the target next to one another is greater). As another example, the capture regions and the oligonucleotide bound to the solid support (or alternatively in solution) may contain non-natural nucleotides, such as isoC and isoG, that pair with each other but not with any of the natural bases. This improves specificity of capture, as the capture regions and the oligonucleotide bound to the support (or alternatively in solution) will not bind to the target nucleic acids at undesirable locations (which would otherwise increase background).

In yet another aspect of the present invention a library may be prepared comprising subsets of the two specific binding partners. Further, members may be selected individually from the library to enable capture of specific or group of specific target sequences. Very high utility for capturing complex and combination targets, such as genetic rearrangements such as in BCR/Abl and prostate cancer fusion regions such as T2:ERG.

The information set forth above is provided to give those of ordinary skill in the art a complete disclosure and description of how to make and use the embodiments of the device and methods, and are not intended to limit the scope of what the inventor regards as his invention. Modifications of the above-described modes (for carrying out the invention that are obvious to persons of skill in the art) are intended to be within the scope of the following claims. All publications, patents, and patent applications cited in this specification are incorporated herein by reference. For example, many of the wash steps cited in the different methods are optional as are some of the steps that remove and/or separate two nucleic acid strands from one another. Not performing at least some of the wash and/or separation steps will afford a faster, simpler and more economical work flow, while still achieving the desired results. In another example, the stepwise addition/binding of certain oligonucleotides and/or target nucleic acids in the exemplified methods may be combined. In addition, the use of tag sequences is optional in some embodiments, and their potential composition may vary from those exemplified above but still within the scope of the knowledge of one skilled in the art. In some cases, the capture oligonucleotides for the tag sequences may be initially bound or may become subsequently bound to a solid support. Furthermore, a variety of polymerases, extension conditions and other amplification protocols known to those skilled in the art may be used in various steps or combination of steps in the methods described above. Other obvious modifications to the methods disclosed that would be obvious to those skilled in the art are also encompassed by this invention.

What is claimed is:

1. A method of immobilizing a target nucleic acid to a solid support, said method comprising the steps of:
   A. mixing a capture oligonucleotide pair containing a first capture and second capture oligonucleotides with a solid support, wherein said capture oligonucleotides each contain a target binding region, a capture region and a stem region, wherein said stem region is located between said target binding and said capture regions, wherein said target binding regions hybridize to adjacent regions of said target nucleic acid, wherein said stem regions are complementary and wherein said capture regions comprise a complementary sequence of a portion of an oligonucleotide bound to said solid support;
   B. annealing said first capture and second capture oligonucleotides to said portion of an oligonucleotide bound to said solid support wherein said stem regions of said capture oligonucleotides hybridize bringing said target regions of said capture oligonucleotides together to produce a single combined nucleic acid sequence wherein said single combined nucleic acid sequence is complementary to said target nucleic acid; and
   C. hybridizing said combined nucleic acid sequence bound to said solid support to said target nucleic acid thereby immobilizing said target nucleic acid to said solid support.

2. A method of immobilizing a target nucleic acid to a solid support, said method comprising the steps of:
   A. mixing a capture oligonucleotide pair containing a first capture and second capture oligonucleotides with said solid support, wherein said capture oligonucleotides each contain a target binding region, a capture region and a stem region, wherein said stem region is located between said target binding and said capture regions, wherein said target binding regions hybridize to adjacent regions of said target nucleic acid, wherein said stem regions are complementary and wherein said capture regions comprise a complementary sequence of a portion of a binding oligonucleotide;
   B. annealing said first capture and second capture oligonucleotides to said portion of an oligonucleotide bound to said solid support wherein said stem regions of said capture oligonucleotides hybridize bringing said target regions of said capture oligonucleotides together to produce a single combined nucleic acid sequence wherein said single combined nucleic acid sequence is complementary to said target nucleic acid; and
   C. hybridizing said combined nucleic acid sequence to said target nucleic acid in solution and immobilizing said target nucleic acid to said solid support, thereby immobilizing said target nucleic acid to said solid support.

3. A method of amplifying and detecting a nucleic acid, said method comprising the steps of:
   A. mixing an oligonucleotide pair containing a first capture oligonucleotide and second capture oligonucleotide with a target nucleic acid, wherein said oligonucleotide pair each contain a target binding region, a region to be amplified and a stem region, wherein said stem region is located between said target binding and said region to be amplified, wherein said target binding regions hybridize to adjacent regions of said target nucleic acid, wherein said stem regions are complementary and wherein said regions to be amplified comprise a complementary sequence of a portion of an oligonucleotide that supports amplification or detection;
   B. annealing said first and second capture oligonucleotides to said target nucleic acid wherein said stem regions of said capture oligonucleotides hybridize bringing said regions to be amplified of said oligonucleotide pair together to produce a combined nucleic acid sequence wherein said combined nucleic acid sequence is complementary to a portion of an oligonucleotide that supports amplification or detection;
   C. hybridizing said combined nucleic acid sequence portion to said oligonucleotide and
   D. amplifying or providing detection of said target nucleic acid.

* * * * *